United States Patent [19]

Sproul et al.

[11] 4,127,808

[45] Nov. 28, 1978

[54] ENGINE CHIP DETECTOR

[75] Inventors: Robert D. Sproul, Groveland; Guillermo E. Todd, Peabody, both of Mass.

[73] Assignee: The United States of America as represented by the Secretary of the Air Force, Washington, D.C.

[21] Appl. No.: 840,354

[22] Filed: Oct. 7, 1977

[51] Int. Cl.² .............................................. G01R 27/02
[52] U.S. Cl. .................................. 324/65 R; 340/505; 340/631
[58] Field of Search ............. 324/65 R; 340/236, 270; 200/61.09, 185

[56] References Cited

U.S. PATENT DOCUMENTS

| 3,422,417 | 1/1969 | Lowe | 340/270 |
| 3,724,474 | 4/1973 | DeVale | 324/65 R X |
| 4,030,028 | 6/1977 | Allender | 324/65 R |

Primary Examiner—Stanley T. Krawczewicz
Attorney, Agent, or Firm—Joseph E. Rusz; Henry S. Miller

[57] ABSTRACT

A transistorized engine chip detection system including a milliammeter to give a visual indication of chip buildup and a full light to operate at a critical preset level, utilizing a voltage divider network, a decrease in resistance in the chip detector will cause an increase in current flow, and subsequent lighting of a warning light. A short circuit or large chip would turn light on and give full scale meter reading, broken or unplugged harness turns light on and gives zero meter reading.

5 Claims, 1 Drawing Figure

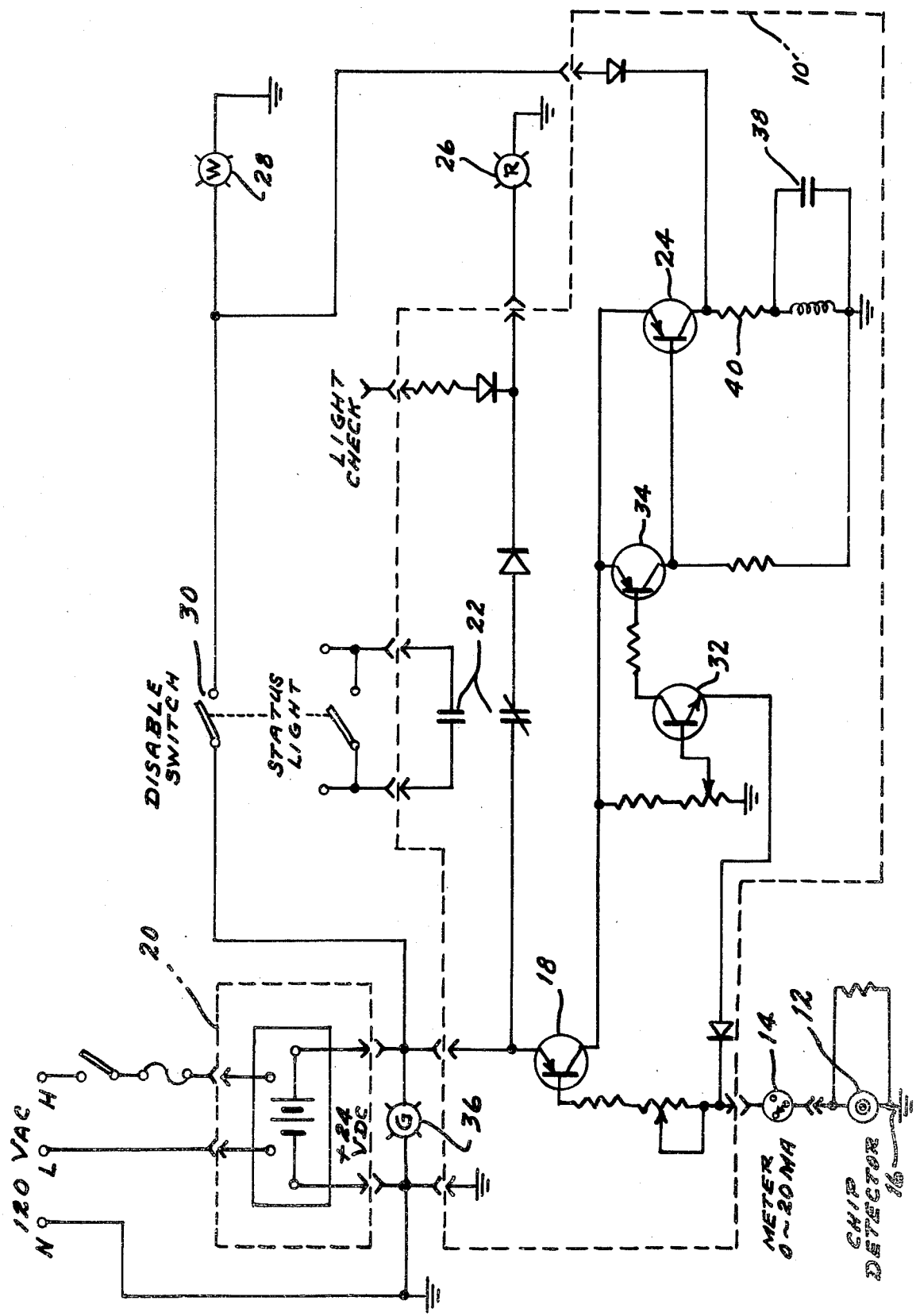

the FIGURE is a circuit diagram of the invention.

ENGINE CHIP DETECTOR

STATEMENT OF GOVERNMENT INTEREST

The invention described herein may be manufactured and used by or for the Government for governmental purposes without the payment of any royalty thereon.

BACKGROUND OF THE INVENTION

This invention relates generally to engine chip detector circuits, and more particularly to a circuit that will detect metal chips in the lubricating oil of engines.

In the normal process of manufacturing engines and in particular aircraft engines, it is customary to operate the engine on a test stand initially to make adjustments and insure the proper installation of parts and accessories. During this operation, frequently metal pieces or chips that have accidently found their way into the engine, appear in the lubricating oil as they are washed out of corners, tubes and blind holes. Some of these metal chips can be tolerated in the system and are quickly filtered out. However, if an excessive amount of this material appears, it could quickly destroy the engine if not detected in sufficient time to shut down the engine.

There currently exists a number of systems that are designed to detect metal chips in the lubricating oil. However, all have certain inherent disadvantages. Generally, these systems are hazardous in that they operate at a high current level for detection. Further, they tend to give false chip indications, causing unnecessary non-scheduled engine shutdowns to investigate. This leads to simply ignoring the indication until a suitable time is available for shutdown, purely for economic reasons. Similarly, prior art systems frequently fail to indicate the existence of chips on many occasions and thereby cause damage to engines. These systems have proven themselves unreliable and nonrepeatable.

SUMMARY OF THE INVENTION

The invention involves a transistorized chip detector circuit which is a completely self-contained unit, including the power supply. The circuit is designed to provide the user with a reliable means and method for detecting foreign magnetic material accumulated on chip detectors of the engine's lubrication system. The circuit detects equivalent chip resistance through the 5.0 to 300 ohm sensitivity range. The circuit provides highly accurate chip detection through a single wire harness which provides the necessary current path to the engine's grounding system. A shunt resistor across the chip detector furnishes this path to "fool-proof" harness hook-up.

The chip detector circuitry is completely transistorized and miniaturized, including a miniaturized milliammeter to give a visual reading of chip buildup prior to actual full light indication at the critical set point for shutdown. Critical set point sensitivity is preadjusted to a selected optimum point.

The invention is designed to operate with a number of identical circuits and are mounted on printed circuit boards and packaged to fit in a conventional rack mount panel. Utilization of a modular power supply ensures optimum performance and reliability.

It is therefore an object of the invention to provide a new and improved engine chip detector.

It is another object of the invention to provide a new and improved engine chip detector for lubricating oils that operates at a low current level.

It is a further object of the invention to provide a new and improved engine chip detector for lubricating oils that is more reliable than any known similar devices.

It is still another object of the invention to provide a new and improved engine chip detector for lubricating oils that avoids giving false chip indications.

It is still a further object of the invention to provide a new and improved engine chip detector for lubricating oils that is compatible with the operation of a plurality of similar devices.

It is another object of the invention to provide a new and improved engine chip detector for lubricating oils that provides an indication of chip buildup before reaching a predesignated shutdown point.

These and other advantages, features and objects of the invention will become more apparent from the following description taken in connection with the illustrative embodiment in the accompanying drawing.

DESCRIPTION OF THE DRAWING

The FIGURE is a circuit diagram of the invention.

DESCRIPTION OF THE PREFERRED EMBODIMENT

Referring now to the Figure, the chip detector utilizes the voltage divider network 10 caused by foreign magnetic material collecting on the chip detector 12. This provides a low current sensing circuit to detect chips. When meter 14 reaches a preset 3 MA, the detector is clean and there are no chips attached. Twenty milliamps, a full scale reading indicates the chip detector gap is filled with a solid chip or many chips. The chip detector circuit will draw a maximum of 25MA under short circuit conditions. The system is adjusted to indicate chip conditions visually when meter 14 reads 15MA which is equivalent to one hundred ohms of material across the chip detector gap.

The cable 16 to the chip detector must be plugged in to provide a ground for switching transistor 18. When power 20 is turned on relay 22 is energized through 18 and 29 which opens the circuit to chip indicator light 26 and closes the interlock circuit to cell status light relay 28. The milliammeter 14 reads about 3 milliamps. If the cable is not plugged into the chip detector, transistor 18 will not turn on to provide power to transistor 24 and relay 22. Light 26 will be on and the cell status lights 28 will be flashing. This condition is recognized by a milliammeter reading of zero . To correct, the harness must be plugged in or the disable switch 30 must be turned on. During normal operation when chips cause the resistance across the chip detector to drop to 100 ohms, trip set point, transistor 32 is turned on which turns on transistor 34, this turns transistor 24 and relay drops out causing light 26 to turn on and cell status light 28 to flash. The milliammeter will read 15 or higher. To reduce meter reading, the chip detector must be cleaned.

The disable switch 30 is a two pole manual toggle switch with one circuit across the relay 22 contacts which is in series with the cell status light relay 22. The other circuit, lights the disable lamp 36 and picks up relay 22. The disable switch can be used to bypass (not correct) a fault at the chip detector or a circuit component failure.

If any harness is broken or unplugged, the respective circuit's chip indicator light turns ON, the external interlock circuit opens and the meter reads ZERO. If chip detection is equivalent to the trip point setting the respective circuit's chip indicator light turns ON, the external interlock circuit opens and the meter reads 15MA. If any harness is short circuited or a chip large enough to produce zero resistance would turn ON the respective circuit indication light and the external interlock circuit would open the meter would read full scale.

Consequently, this system would not only monitor chips in the lube systems, but also maintain an open-loop circuit check and give an indication of the problem.

Although the invention has been described with reference to a particular embodiment, it will be understood by those skilled in the art that the invention is capable of a variety of alternative embodiments within the spirit and scope of the appended claims.

What is claimed is:

1. An engine chip detection system comprising: a power supply; a chip detection means; electrical circuit means connecting the power supply and chip detection means including, a voltage divider network, means for sensing a decrease in resistance and gate means for switching on a signal means, means for presetting the threshold level of the said gate means, means for isolating transient signals of less than a predetermined period of duration, and means for sensing and identifying an open circuit.

2. An engine chip detection system according to claim 1 wherein said signal means is a lamp.

3. An engine chip detection system according to claim 2 wherein said signal means further includes a milliammeter.

4. An engine chip detection system according to claim 3 wherein said means for isolating is a time delay noise discriminator.

5. An engine chip detection system according to claim 4 including means for bypassing one chip detector without disabling the entire system.

* * * * *